United States Patent
Park et al.

(10) Patent No.: US 10,371,616 B2
(45) Date of Patent: *Aug. 6, 2019

(54) AIRBORNE MICROBIAL MEASUREMENT APPARATUS AND METHOD

(71) Applicant: LG ELECTRONICS INC., Seoul (KR)

(72) Inventors: Chulwoo Park, Seoul (KR); Sunghwa Lee, Seoul (KR); Yeekyeong Jung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 176 days.

This patent is subject to a terminal disclaimer.

(21) Appl. No.: 15/120,728

(22) PCT Filed: Dec. 12, 2014

(86) PCT No.: PCT/KR2014/012275
§ 371 (c)(1),
(2) Date: Aug. 22, 2016

(87) PCT Pub. No.: WO2015/130000
PCT Pub. Date: Sep. 3, 2015

(65) Prior Publication Data
US 2017/0059466 A1    Mar. 2, 2017

(30) Foreign Application Priority Data
Feb. 27, 2014 (KR) .................. 10-2014-0023204

(51) Int. Cl.
*G01N 1/22* (2006.01)
*C12Q 1/04* (2006.01)
(Continued)

(52) U.S. Cl.
CPC .......... *G01N 15/0625* (2013.01); *C12Q 1/04* (2013.01); *C12Q 1/06* (2013.01); *C12Q 1/24* (2013.01);
(Continued)

(58) Field of Classification Search
CPC .......... C12Q 1/24; C12Q 1/05; C12Q 1/2202; G01N 1/22; G01N 21/763; G01N 21/645
See application file for complete search history.

(56) References Cited

U.S. PATENT DOCUMENTS

| 4,301,002 A | 11/1981 | Loo |
| 5,040,424 A | 8/1991 | Marple et al. |

(Continued)

FOREIGN PATENT DOCUMENTS

| CN | 101351736 A | 1/2009 |
| EP | 0 964 101 A1 | 12/1999 |

(Continued)

OTHER PUBLICATIONS

Daniel Verreault et al., "Methods for Sampling of Airborne Viruses", Microbiology and Molecular Biology Reviews, vol. 72, No. 3, Sep. 2008, pp. 413-444.

*Primary Examiner* — Michael L Hobbs
(74) *Attorney, Agent, or Firm* — Dentons US LLP

(57) ABSTRACT

Provided is an airborne microbial measurement apparatus and a method of measuring the same. The airborne microbial measurement apparatus includes a particle separation device comprising an introduction part for introducing air and a nozzle part disposed on one side of the introduction part, a microbial particle passage through which microbial particles in the air passing through an inner passage of the nozzle part flow, an air particle passage through which air particles in the air passing through an outer space of the nozzle part flow, a collection device communicating with the microbial particle passage, the collection device comprising a filter part onto which the microbial particles are collected, and a luminescence measurement device dispose on one side of the collection device to detect an amount or intensity of light emitted from the microbial particles collected onto the filter part.

10 Claims, 4 Drawing Sheets

(51) Int. Cl.
  *G01N 15/06* (2006.01)
  *C12Q 1/24* (2006.01)
  *G01N 21/76* (2006.01)
  *C12Q 1/06* (2006.01)
  *G01N 15/00* (2006.01)

(52) U.S. Cl.
  CPC ......... *G01N 1/2205* (2013.01); *G01N 1/2208* (2013.01); *G01N 15/00* (2013.01); *G01N 15/0643* (2013.01); *G01N 21/763* (2013.01); *G01N 2015/0019* (2013.01); *G01N 2015/0069* (2013.01)

(56) References Cited

U.S. PATENT DOCUMENTS

| | | | |
|---|---|---|---|
| 10,092,873 B2 * | 10/2018 | Jung | B01D 46/442 |
| 2003/0042428 A1 | 3/2003 | Peukert et al. | |
| 2005/0247868 A1 | 11/2005 | Call et al. | |
| 2007/0107539 A1 | 5/2007 | Bell et al. | |
| 2010/0165341 A1 | 7/2010 | Babico et al. | |
| 2011/0183371 A1 | 7/2011 | Noda et al. | |
| 2012/0045752 A1 | 2/2012 | Ensor et al. | |
| 2012/0257192 A1 | 10/2012 | Jiang | |
| 2012/0295301 A1 | 11/2012 | Miyashita et al. | |
| 2013/0000422 A1 | 1/2013 | Miyashita et al. | |
| 2013/0199234 A1 | 8/2013 | Kim et al. | |
| 2013/0319239 A1 | 12/2013 | Takenaka et al. | |
| 2014/0017723 A1 | 1/2014 | Hwang et al. | |

FOREIGN PATENT DOCUMENTS

| | | |
|---|---|---|
| JP | 2008-500528 A | 1/2008 |
| JP | 2008-261712 A | 10/2008 |
| JP | 2011-506764 A | 3/2011 |
| JP | 2011-169903 A | 9/2011 |
| JP | 2012-217382 A | 11/2012 |
| JP | 2013-2947 A | 1/2013 |
| JP | 2013-170972 A | 9/2013 |
| JP | 2013170969 A | 9/2013 |
| KR | 10-2005-0019256 A | 3/2005 |
| WO | 2009/157510 A1 | 12/2009 |
| WO | 2012165036 A1 | 12/2012 |

\* cited by examiner

[Fig. 1]
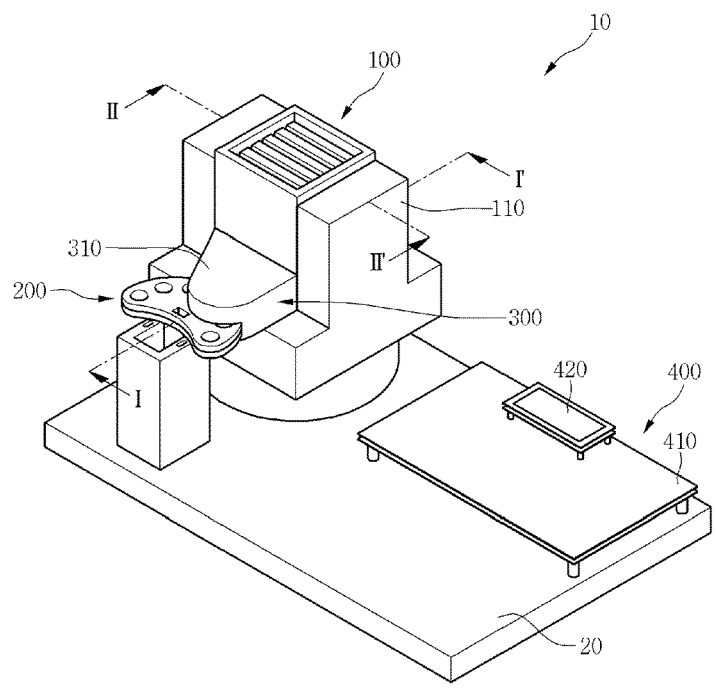
[Fig. 2]
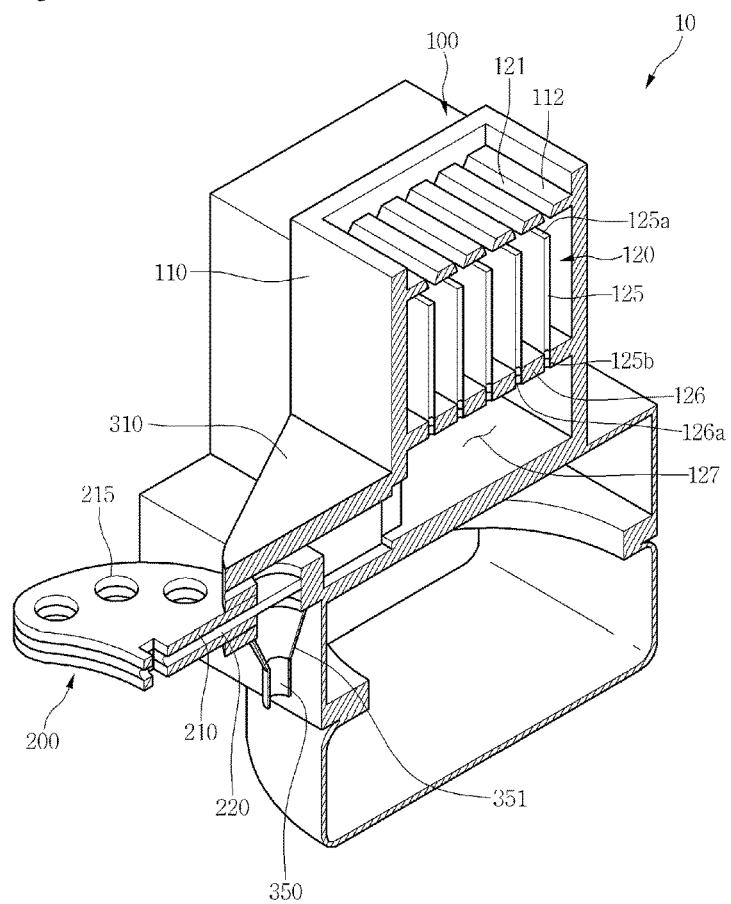

[Fig. 3]
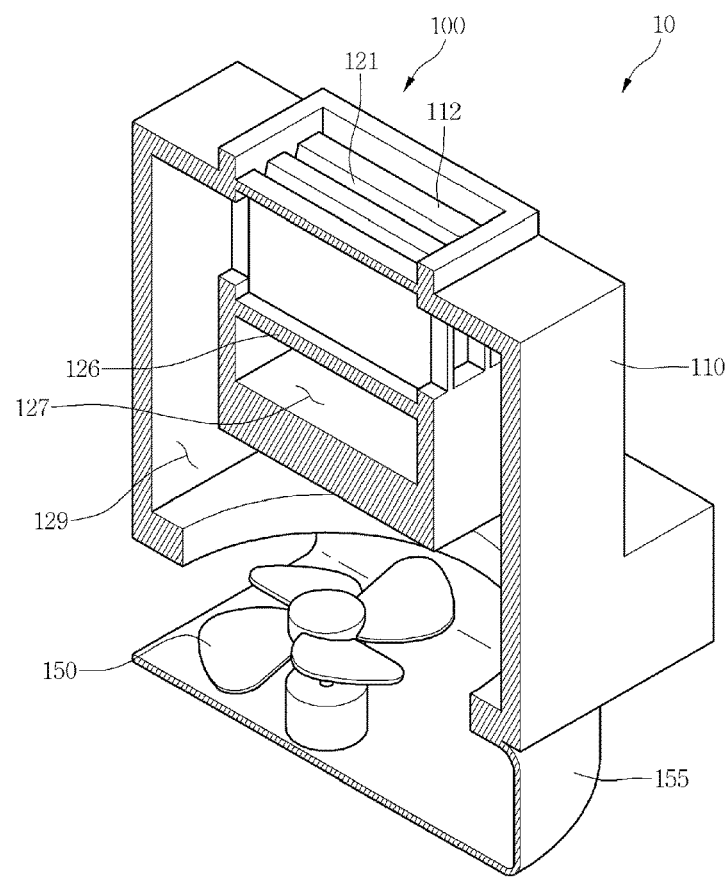
[Fig. 4]
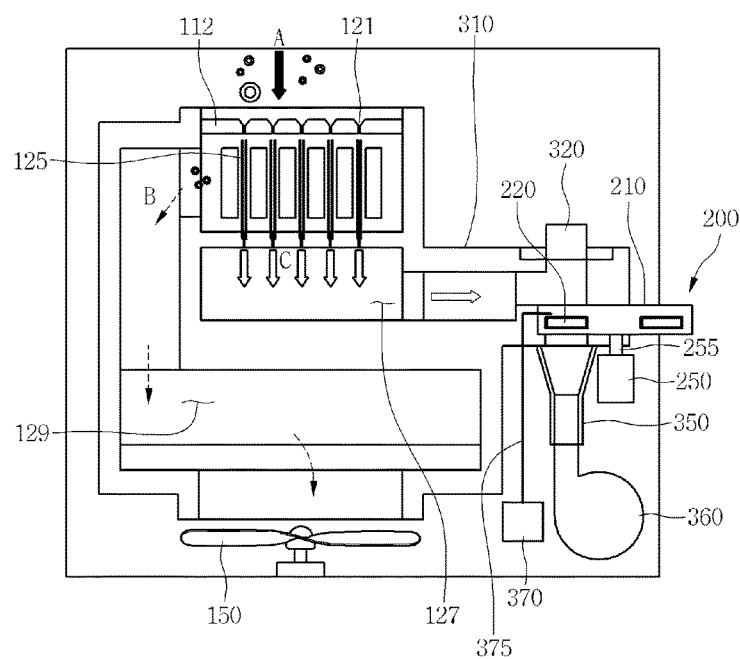

[Fig. 5]
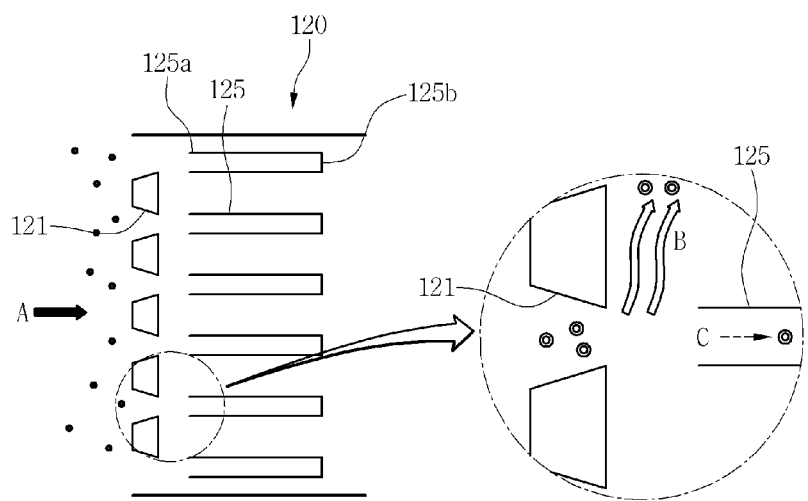
[Fig. 6]
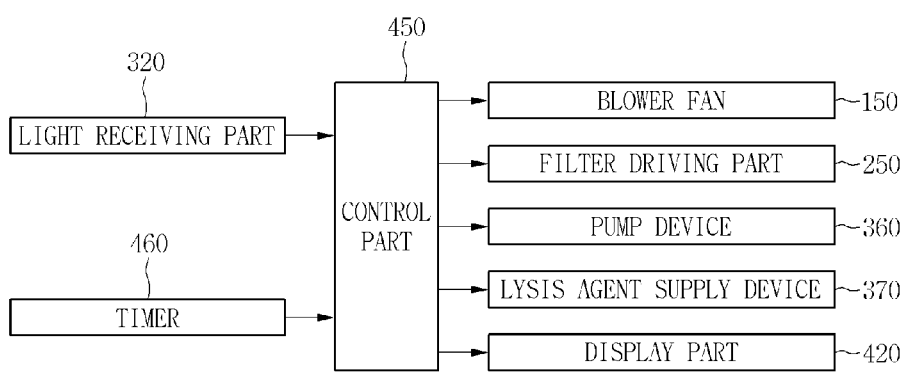

[Fig. 7]
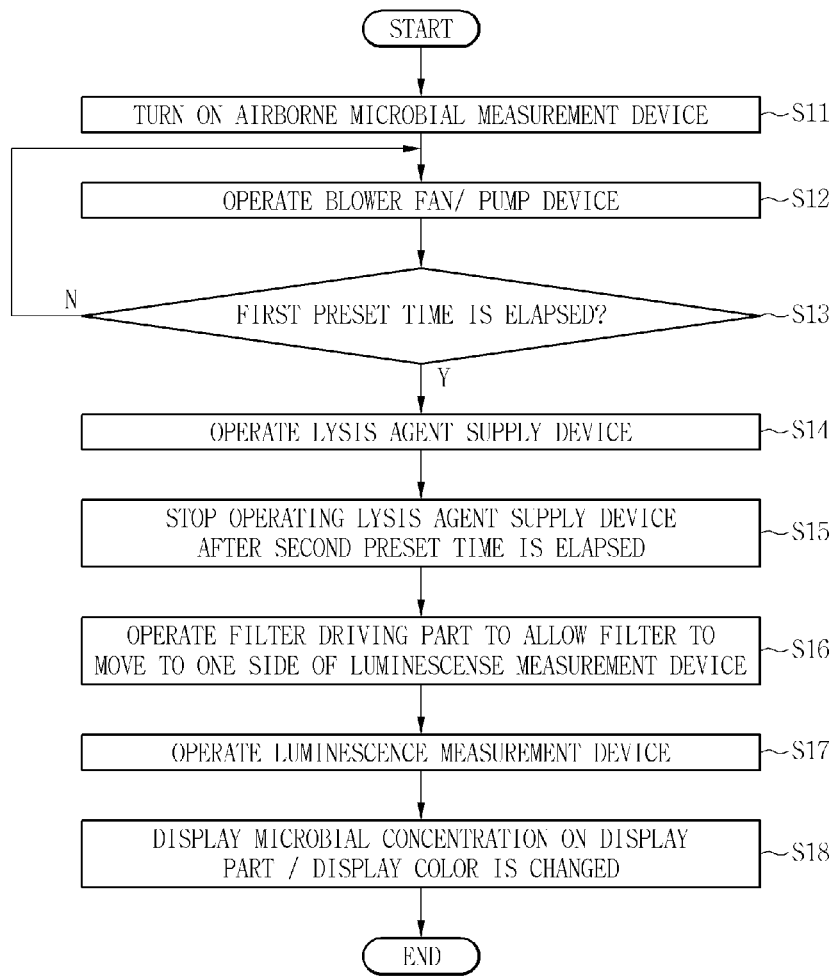
[Fig. 8]
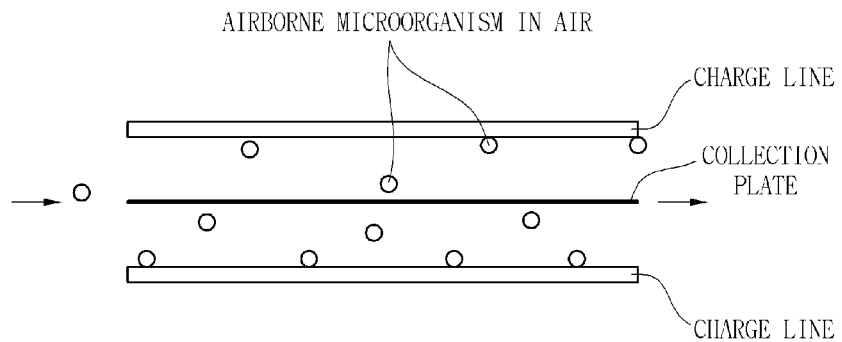

AIRBORNE MICROBIAL MEASUREMENT APPARATUS AND METHOD

This application is a National Stage Application of International Application No. PCT/KR2014/012275, filed on Dec. 12, 2014, which claims the benefit of Korean Patent Application No. 10-2014-0023204, filed on Feb. 27, 2014, all of which are hereby incorporated by reference in their entirety for all purposes as if fully set forth herein.

TECHNICAL FIELD

The present disclosure relates to an airborne microbial measurement apparatus and method.

BACKGROUND ART

In recent years, as avian influenza and new type influenza are issued, aerial infection problems are becoming the main issue of society. For this reason, the subject with regard to a method of measuring airborne microbial particles in air is importantly treated, and a biosensor market is sharply growing accordingly.

As the existing method of measuring airborne microbial particles in air, there are a culture method in which airborne bioparticles in a sample gas are collected onto a surface of a solid or liquid suitable for growth to culture the collected bioparticles under an appropriate temperature-humidity condition for a predetermine time, thereby calculating the number of collected microorganism from the number of colony generated on the surface and a staining method in which bioparticles are stained to measure the number of microorganism by using a fluorescence microscope.

Recently, an adenosine triphosphate (ATP) bioluminescence method using a principle in which ATP reacts with luciferin/luciferase to emit light may be developed to allow a series of processes including ATP elimination process, ATP extraction, and luminescence amount measurement to be performed within about thirty minutes, thereby implementing rapid working.

However, according to the above-described methods, the airborne microbial particles existing in the air may not be measured in real time, and a series of handworks including a separate sampling process and pretreatment process is required. Thus, there is a limitation in that a system of automatically measuring the airborne microbial particles in the air can not be developed by using these methods.

FIG. 8 is a view of an electric dust collector provided in an airborne microbial measurement apparatus according to a related art.

Referring to FIG. 8, an electric dust collector according to the related art includes collection plates disposed on both sides thereof and a charge line (a discharge electrode) disposed between the collection plates disposed on both sides thereof.

When a high voltage is applied to the charge line, corona discharge occurs to generate ions. Here, predetermined particles in a gas are charged by the generated ions. Also, the charged particles may move and be collected to a dust collection electrode (the collection plate) by an electric force. That is, the electric dust collector may be understood as a dust collecting device that is capable of collecting predetermined particles using an electrostatic principle. The predetermined particles may include foreign substances such as dusts or airborne microorganism.

The airborne microbial measurement apparatus according to the related art includes the electric dust collector and a collection rod for collecting the microorganism collected onto the collection plate. In the airborne microbial measurement apparatus according to the related art, when the airborne microorganism is collected onto the collection plate by driving of the electric dust collector, a user manually put the collection rod into contact with the collection plate to collect or sample the airborne microorganism. Also, the collected airborne microorganism reacts with a lysis reagent to emit light. Here, the measurement apparatus detects the emitted light to measure a concentration of the microorganism.

Like this, in the case of the airborne microbial measurement apparatus according to the related art, since the collection rod has to be separately provided, and also the user has to collect the airborne microorganism collected onto the collection plate by using the collection rod, it takes a lot of time and also comes expensive.

DISCLOSURE OF INVENTION

Technical Problem

Embodiments provide an airborne microbial measurement apparatus and method that are capable of rapidly measuring an airborne microbialparticles existing in air.

Solution to Problem

In one embodiment, an airborne microbial measurement apparatus includes: a particle separation device comprising an introduction part for introducing air and a nozzle part disposed on one side of the introduction part; a microbial particle passage through which microbial particles in the air passing through an inner passage of the nozzle part flow; an air particle passage through which air particles in the air passing through an outer space of the nozzle part flow; a collection device communicating with the microbial particle passage, the collection device including a filter part onto which the microbial particles are collected; and a luminescence measurement device dispose on one side of the collection device to detect an amount or intensity of light emitted from the microbial particles collected onto the filter part.

The airborne microbial measurement apparatus may further include: a pump device generating a flow of the microbial particles in the microbial particle passage; and a blower fan generating a flow of the air particles in the air particle passage.

The nozzle part may include: an inlet into which the microbial particles in the air are introduced; and an outlet through which the microbial particles are discharged to the microbial particle passage.

The inlet may be disposed to be spaced apart from the introduction part in one direction, and the air particles may be introduced into the air particle passage through a space between the inlet and the introduction part.

The introduction part may include a plurality of slits, and the nozzle part is provided in plurality to correspond to the number of plurality of slits.

The airborne microbial measurement apparatus may further include a partition plate having a communication hole to which the outlet of the nozzle part is coupled and separating the microbial particle passage from the air particle passage.

The collection device may include: a filter case in which the filter part is accommodated; and a plurality of filter holes defined in the filter case to communicate with the microbial particle passage.

The airborne microbial measurement apparatus may further include a filter driving part rotating the filter part or the filter case, wherein, when the filter driving part operates in the state where one of the plurality of filter holes communicates with the microbial particle passage, the other one of the plurality of filter holes may be disposed to communicate to the microbial particle passage.

The luminescence measurement device may further include a light receiving part for detecting the light emitted from the filter part, wherein, when the filter driving part operates, the one filter hole may be disposed to face the light receiving part.

The airborne microbial measurement apparatus may further include a lysis agent supply device for supplying a lysis reagent to the filter part; and a luminous material disposed on the filter part.

The airborne microbial measurement apparatus may further include a display part for displaying information with respect to a concentration of the microbial particles on the basis of information relating to the amount or intensity of the light detected by the luminescence measurement device.

In another embodiment, an airborne microbial measurement method includes: introducing air into a particle separation device to separate airborne microbial particles in the air from air particles except for the airborne microbial particles; collecting the airborne microbial particles onto a filter part; lysing the airborne microbial particles collected onto the filter part to allow the lysed airborne microbial particles to react with a luminous material; and detecting an amount or intensity of light emitted by reaction between the lysed airborne microbial particles and the luminous material by using a luminescence measurement device, wherein, in the separating of the airborne microbial particles in the air from the air particles, the airborne microbial particles flow through an inner passage of a nozzle part, and the air particles flow through an outer space of the nozzle part.

A pump device and a blower fan may be driven so as to separate the airborne microbial particle from the air particles.

When the pump device and the blower fan may be driven for a first preset time, a lysis reagent may be supplied onto the filter part to lyse the airborne microbial particles.

When the lysis reagent is supplied onto the filter part for a second preset time, a filter driving part for rotating the filter part may operate to allow the airborne microbial particles to be disposed at one side of the luminescence measurement device.

In further another embodiment, an airborne microbial measurement apparatus includes: a particle separation device including a nozzle part through which microbial particles in air flow; a microbial particle passage through which the microbial particles passing through the nozzle part flow; an air particle passage through which remaining particles in the air except for the microbial particles flow; a flow generation device allowing a flow into the microbial particle passage or the air particle passage to be generated; a filter part communicating with the microbial particle passage to collect the microbial particles thereon; a lysis agent supply device supplying a lysis reagent for lysing the microbial particles into the filter part; and a luminescence measurement device for detecting an amount or intensity of light emitted from the microbial particles collected onto the filter part.

The flow generation device may include: an air pump allowing the flow into the microbial particle passage to be generated; and a fan allowing the flow into the air particle passage to be generated.

The airborne microbial measurement apparatus may further include a filter case in which the filter part is accommodated; and a plurality of filter holes defined in the filter case to communicate with the microbial particle passage, wherein the filter part may be exposed to the outside through the plurality of filter holes.

The airborne microbial measurement apparatus may further include a luminous material disposed in the filter part to react with adenosine triphosphate (ATP) of the microbial particles extracted by the lysis reagent, thereby emitting light.

The airborne microbial measurement apparatus may further include a display part displaying information with respect to a concentration of the microbial particles on the basis of information relating to an amount or intensity of the light detected by the luminescence measurement device, wherein the display part may include a lighting unit displaying colors different from each other depending on the concentration of the microbial particles.

Advantageous Effects of Invention

According to the airborne microbial measurement apparatus and method, the airborne microbial particles in the air may be automatically separated from the air through the virtual impactor structure without manually sampling the airborne microbial particles collected onto the collection plate by the user, and thus the process for separating particles may be easily performed to reduce the time taken to perform the process.

Also, when the separated microbial particles are collected in the collection device or the filter part, the filter part moves toward the luminescence measurement device detect the luminescence amount according to the reaction with the microbial particles, and thus the luminescence amount may be automatically successively measured from the particle separation process to the light emission measurement process.

Also, since the luminous material is applied onto the collection device or the filter part, and the microbial lysis reagent is supplied to the collection device or the filter part, the luminescence measurement process may be easily performed.

Also, the main flow in which the relatively small particles flow and the sub flow in which the relatively large particles flow may be effectively separated from each other by the virtual impactor structure. Also, since the fan is used as the driving part at the main flow side where the pressure loss is relatively low, and the low flow rate pump is used as the driving part at the sub flow side where the pressure loss is relatively high, the airborne microbial measurement apparatus may not increase in volume and weight.

Also, since the display part displaying the information with respect to the microbial concentration on the basis of the light luminescence amount detected in the luminescence measurement device is further provided to display the warning sign when the microbial concentration is higher than the predetermined concentration, the user convenience may increase.

BRIEF DESCRIPTION OF DRAWINGS

FIG. 1 is a perspective view of an airborne microbial measurement apparatus according to an embodiment.

FIG. 2 is a cross-sectional view taken along line I-I' of FIG. 1.

FIG. 3 is a cross-sectional view taken along line II-II' of FIG. 1.

FIG. 4 is a schematic view of inner constitutions of the airborne microbial measurement apparatus according to an embodiment.

FIG. 5 is a schematic view of a nozzle part according to an embodiment.

FIG. 6 is a block diagram of the airborne microbial measurement apparatus according to an embodiment.

FIG. 7 is a flowchart illustrating a method of measuring the airborne microbial by using the airborne microbial measurement apparatus according to an embodiment.

FIG. 8 is a view of an electric dust collector provided in an airborne microbial measurement apparatus according to a related art.

MODE FOR THE INVENTION

Hereinafter, reference will now be made in detail to the embodiments of the present invention, examples of which are illustrated in the accompanying drawings. The invention may, however, be embodied in many different forms and should not be construed as being limited to the embodiments set forth herein; rather, that alternate embodiments included in other retrogressive inventions or falling within the spirit and scope of the inventive concept will fully convey the concept of the invention to those skilled in the art.

FIG. 1 is a perspective view of an airborne microbial measurement apparatus according to an embodiment, FIG. 2 is a cross-sectional view taken along line I-I' of FIG. 1, and FIG. 3 is a cross-sectional view taken along line II-II' of FIG. 1.

Referring to FIGS. 1 to 3, the airborne microbial measurement apparatus according to an embodiment includes a base 20 and a plurality of devices disposed at an upper side of the base 20. The plurality of devices include a particle separation device 100 for suctioning air to separate airborne microbial particles from the air and a collection device 200 in which the airborne microbial particles separated by the particle separation device 100 are collected.

Also, the plurality of devices may further include a luminescence measurement device 300 disposed at one side of the collection device 200 to detect an amount or intensity of light emitted from the airborne microbial and a control device 400 electrically connected to the luminescence measurement device 300. The control device 400 includes a printed circuit board (PCB) 410 on which a plurality of circuit components are disposed and a display part 420 disposed on the PCB 410 to display information relating to concentration of the airborne microbial particles.

In detail, the particle separation device 100 includes a first housing 110 defining a predetermined inner space and a top surface part 112 coupled to an upper portion of the first housing 110. A plurality of slits 121 are defined in the top surface part 112 as an "air introduction part" into which the air existing outside the particle separation device 100 is suctioned.

The slit 121 may have a width of several mm. Also, since the slit 121 is defined in plurality in the top surface part 112, the air introduced through the slit 121 may have a low resistance, i.e., a low differential pressure between the inside and outside of the slit 121. Thus, the air introduced through the plurality of slits 121 may secure a sufficient flow rate.

A nozzle part 120 through which the air introduced through the slit 121 passes may be provided in the first housing 110. That is, the nozzle part 120 may be disposed in an inner space of the first housing 110. Also, the nozzle part 120 is spaced apart downward from the slit 121 to extend downward.

The nozzle part 120 may be provided in plurality to correspond to the number of the plurality of slits 121. Here, the plurality of the nozzle parts 120 may be spaced apart from each other. Also, the plurality of nozzle part 120 may be disposed at a lower side of the plurality of the slits 121 to correspond to positions of the plurality of slits 121. For example, as illustrated in FIG. 2, the plurality of nozzle parts 120 may be disposed spaced apart from each other in a horizontal direction.

The nozzle part 120 includes an inner passage 125 through which airborne microbial particles in the air introduced into the first housing 110 through the slit 121 flows. The inner passage 125 defines an inner space of the nozzle part 120.

An inlet part 125a defining one end of the nozzle part 120 and through which the airborne microbial is introduced into the inner passage 125 may be defined in the inner passage 125. For example, the inlet part 125a is defined on an upper end of the inner passage 125. The airborne microbial particles in the air introduced through the slit 121 may flow in the inner passage 125 through the inlet part 125a. Air particles from which the airborne microbial particles is separated may flow in an outer space of the inner passage 125 to pass through an air particle passage 129.

Also, an outlet part 125b defining the other end of the nozzle part 120 and through which the airborne microbial particles flowing in the inner passage 125 is discharged from the nozzle part 120. For example, the outlet part 125b is defined on a lower end of the inner passage 125.

A microbial particle passage 127 in which the airborne microbial particles discharged through the outlet part 125b flows may be defined at one side of the outlet part 125b. The air particle passage 129 may be called a first passage or a main flow passage. Also, the microbial particle passage 127 may be celled a second passage or a sub flow passage.

A partition plate 126 for partitioning the air particle passage 129 from the microbial particle passage 127 may be disposed on a lower end of the nozzle part 120. The lower end of the nozzle part 120, i.e., the outlet part 125b may be coupled to the partition plate 126. In detail, a communication hole 126a communicating with the outlet part 125b is defined in the partition plate 126. The communication hole 126a is defined to pass through upper and lower portions of the partition plate 126.

The outlet part 125b is coupled to the communication hole 126a within the partition plate 126. Also, the outlet part 125b may communicate with the microbial particle passage 127 through the communication hole 126a. Since the air particle passage 129 and the microbial particle passage 127 is separated from each other by the partition plate 126, mixture of a particle in the air particle passage 129 and a particle in the microbial particle passage 127 may be prevented.

A second housing 310 in which the luminescence measurement device 300 is disposed is provided at one side of the first housing 110. The microbial particle passage 127 may extend from the partition plate 126 toward the collection device 200. An inner space of the second housing 310 may define at least one portion of the microbial particle passage 127.

A filter case 210 in which a filter part 220 is accommodated and a plurality of filter holes 215 defined in the filter case 210 are provided in the collection device 200. The filter part 220 may be exposed to the outside through the plurality of filter holes 215. Also, the microbial particles flowing through the microbial particle passage 127 may be collected onto the filter part 220 through one of the plurality of filter holes 215.

The plurality of filter holes 215 includes one filter hole communicating with the microbial particle passage 127 and the other filter hole communicating with the microbial particle passage 127 when the filter case 210 rotates. When the other filter hole communicates with the microbial particle passage 127, the one filter hole may face a light receiving device 320.

The filter part 220 may be fixed to an inside of the filter case 210. Also, the filter case 210 may be rotatable.

A filter driving part 250 for providing a rotation force to the filter case 210 is disposed at one side of the filter case 210. For example, the filter driving part 250 may be a motor. A rotation shaft (see reference numeral 255 of FIG. 4) may extend from the filter driving part 250 to the filter case 210.

When the filter driving part 250 is driven, the rotation shaft 255 rotates. Here, the filter case 210 may rotate in a clockwise or counterclockwise direction by the rotation shaft (see reference numeral 255 of FIG. 4). Also, the filter part 220 may rotate together with the filter case 210.

When the filter part 220 is disposed at one position, the one filter hole 215 communicates with the microbial particle passage 127. Thus, the microbial particles flowing through the microbial particle passage 127 may be collected onto the filter part 220 through the one filter hole 215. Here, one area of the filter part 220 in which the microbial particles are collected may correspond to an area that is exposed to the microbial particle passage 127 by the one filter hole 215.

Also, when the filter part 220 rotates, the other filter hole 215 communicates with the microbial particle passage 127. Here, the one filter hole 215 may be disposed at one side of the luminescence measurement device 330.

A pump device 360 driven to flow the microbial particles and a pump connection part 350 extending from the filter case 210 to the pump device 360 are disposed at one side of the collection device 200. The pump device 360 may include an air pump. A portion of the particles in the microbial particle passage 127 except for the microbial particles collected onto the filter part 220, e.g., air particles may flow into the pump device 360 via the pump connection part 350.

The pump connection part 350 includes a cyclone unit 351 of which a flow cross-sectional area is gradually reduced from the filter case 210 toward the pump device 360. The air may increase in flow rate while passing through the cyclone unit 351 and be introduced into the pump device 360.

The pump device 360 may be understood as a device having an advantage over a fan in that the pump device secures a predetermined suction flow rate even though pressure loss occurs. Thus, the pump device 360 may be used to allow a flow of the particles in the microbial particle passage 127 to be generated, thereby improving suction efficiency even though pressure loss occurs in the nozzle part 120 or the filter part 220. Also, since the flow rate of the particles in the microbial particle passage 127 is relatively low, a low-flow rate pump may be applied as the air pump. Therefore, a phenomenon in which the airborne microbial measurement device increases in volume or weight may be prevented.

The luminescence measurement device 300 includes the light receiving part 320 disposed at one side of the collection device 200 to accommodate the light emitted from the microbial particles. For example, at least one portion of the light receiving part 320 may be disposed in the second housing 310.

When the filter case 210 rotates after the microbial particles are collected onto the filter part 220 through the one filter hole 215, the one filter hole 215 may face the light receiving part 320. The light receiving part 320 may detect an amount or intensity of light emitted from the microbial particles in the filter part 220.

The airborne microbial measurement apparatus 10 may further include a lysis agent supply device 370 for supplying a lysis reagent into the filter part 220 and a supply passage 375 extending from the lysis agent supply device 370 to one filter hole 215 or the filter part 220. The lysis reagent may be understood as a lysis agent for lysing cells (or cell walls) of the airborne microbial particles collected onto the filter part 220. When the cells of the airborne microbial particles react with the lysis reagent, adenosine triphosphate (ATP) is extracted.

Also, a luminous material may be applied onto the filter part 220. The luminous material may be understood as a material for emitting the light by reacting with the ATP of the microbial particles which is extracted by the lysis reagent. The luminous material includes luciferin and luciferase. The luciferin is activated by the ATP existing in the lysed cell to change into active luciferin. The active luciferin is oxidized by the effect of the luciferase that is a luminous enzyme to become oxide luciferin. Here, chemical energy is converted into light energy to emit the light.

The air particle passage 129 through which particles each of which has a relatively small size separated from the airborne microbial particles at an inlet-side of the nozzle part 120, e.g., the air particles flow may be defined in the first housing 110. The particle within the air particle passage 129 may have a size less than that of the particle within the microbial particle passage 127. However, the flow rate in the air particle passage 129 may be greater than that in the microbial particle passage 127.

The air particle passage 129 may be separated from the microbial particle passage 127 by the partition plate 126 to extend toward a blower fan 150. The blower fan 150 is a device for allowing a flow into the air particle passage 129 to be generated. For example, the blower fan 150 may be accommodated within a fan housing 155. The fan housing 155 is disposed on a lower portion of the first housing 110.

Also, the blower fan 150 may be understood as a device that is capable of securing a sufficient flow rate when the pressure loss is low when compared to the air pump. Thus, the blower fan 150 is provided in a passage where the pressure loss is low such as the air particle passage 129 to allow a sufficient air particle flow to be generated (main flow). The pump device 360 may be called "flow generation device" together with the blower fan 150.

FIG. 4 is a schematic view of inner constitutions of the airborne microbial measurement apparatus according to an embodiment, and FIG. 5 is a schematic view of a nozzle part according to an embodiment.

An operation of the airborne microbial measurement apparatus according to an embodiment will be simply described with reference to FIGS. 4 and 5.

When the pump device 360 and the blower fan 150 are driven, the air (see reference symbol A of FIG. 5) existing outside the airborne microbial measurement apparatus 10 is introduced into the first housing 110 through the plurality of slits 121 in the top surface part 112.

The air may increase in flow rate while passing through the plurality of slits 121 due to the narrow cross-sectional area of the passage. The airborne microbial particles having relatively large sizes in the air passing through the plurality of slits 121 may be introduced into the inner passage 125 through the inlet part 125a of the nozzle part 120 (see reference symbol C of FIG. 5). Also, the airborne microbial particles may be discharged from the inner passage 125 trough the outlet part 125b to flow the microbial particle passage 127 through the communication hole 126a of the partition plate 126.

On the other hand, the air particles having relatively small sizes in the air passing through the plurality of slits 121 may be changed in traveling direction (see reference symbol B of FIG. 5). Thus, the air particles does not flow into the inner passage 125 but flow along the outer space of the nozzle part 120. Also, the air particles flow through the air particle passage 129 to pass through the blower fan 150. As described above, the flow rate of the air particles may be greater than that of the microbial particles.

That is, in the process in which the air flows through the nozzle having the narrow cross-section, the airborne microbial particle having a relatively large size may be introduced into the inner passage 125 through the inlet part 125a. Also, the air particle having a relatively small size may be changed in traveling direction to flow in a stream line through a space between the slit 121 and the inlet part 125a, thereby flowing through the air particle passage 129.

The particle separation structure may be called a virtual impactor structure. In the current embodiment, since the virtual impactor structure is applied, the airborne microbial particles may be easily separated from the air particles.

The airborne microbial particles flowing through the microbial particle passage 127 may flow into the collection device 200 and be collected on the one area of the filter part 220 via the one filter hole 215 of the filter case 210.

This collection process is performed during a preset time, and then the lysis reagent is supplied from the lysis agent supply device 370 into the filter part 220. The microbial particles collected onto the filter part 220 may be lysed by the lysis reagent to extract the ATP, thereby reacting with the luminous material applied onto the filter part 220.

Also, the filter driving part 250 is driven to rotate the filter case 210. Thus, the one filter hole 215 is disposed at one side of the luminescence measurement device 300 to face the light receiving part 320, and the other filter hole 215 is disposed to communicate with the microbial particle passage 127. Therefore, when the next collection process is performed, the microbial particles flowing through the microbial particle passage 127 may be collected on the other area of the filter part 220 via the other filter hole 215 of the filter case 210.

Like this, by the driving of the filter driving part 250, the one area of the filter part 220 in which the microbial particles are collected moves to face the luminescence measurement device 300 or the light receiving part 320, and the other area of the filter part 220 moves to a position where the filter part 220 communicates with the microbial particle passage 127 to collect the microbial particles. Thus, since the filter case 210 and the filter part 220 are rotatable, the microbial collection process and the luminescence process may be automatically conducted.

When the ATP reacts with the luminous material, predetermined light may be emitted. Here, the light receiving part 320 may detect the amount or intensity of the emitted light.

FIG. 6 is a block diagram of the airborne microbial measurement apparatus according to an embodiment, and FIG. 7 is a flowchart illustrating a method of measuring the airborne microbial by using the airborne microbial measurement apparatus according to an embodiment.

Referring to FIG. 6, the airborne microbial measurement apparatus 10 according to an embodiment includes the pump device 360 allowing the flow of the airborne microbial particles to be generated and the blower fan 150 allowing the flow of the air particles to be generated.

Also, the airborne microbial measurement apparatus 10 may further include the filter driving part 250 for rotating the filter case 210 and the filter part 220 and the lysis agent supply device 370 for supplying lysis reagent into the filter 220.

The airborne microbial measurement apparatus 10 includes the display part 420 on which information with respect to concentration of the airborne microbial particles collected onto the filter part 220. The display part 420 may include a lighting unit displayed with different colors depending on concentration values of the airborne microbial particles. For example, the lighting unit may include a first lighting part displayed with a green color when the airborne microbial particles have a low concentration value, a second lighting part displayed with a yellow color when the airborne microbial particles have a middle concentration value, and a third lighting part displayed with a red color when the airborne microbial particles have a high concentration value. For another example, the first to third lighting units may be provided as one lighting part.

The airborne microbial measurement apparatus 10 includes the light receiving part 320 detecting the amount of light emitted from the microbial particles collected onto the filter part 220 and a timer 460 integrating an elapsing time in the process for collecting the microbial particles and the process for supplying the lysis reagent.

Information detected by the light receiving part 320 or the timer 460 may be transmitted to the control part 450. The control part 450 may control of operations of the pump device 360, the blower fan 150, the filter driving part 250, the lysis agent supply device 370, and the display part 420 on the basis of the transmitted information.

Referring to FIG. 7, when the airborne microbial measurement apparatus 10 is turned on to operate the blower fan 150 and the pump device 360, the air outside the airborne microbial measurement apparatus 10 may be introduced into the first housing 110 through the plurality of slits 121. Also, the airborne microbial particles may be separated from the air particles to respectively flow in the microbial particle passage 127 and the air particle passage 129 by the virtual impactor structure within the first housing 110. In operations S11 and S12, the particles flowing through the microbial particle passage 127 may be collected onto the filter part 220.

This collecting process may be performed during a first preset time. In operation S13, the elapsing time is integrated by the timer 460, and the control part 450 recognizes whether the first preset time elapses.

When the first preset time elapses, the blower fan 150 and the pump device 360 stop driving. Then, the lysis agent supply device 370 operates to supply the lysis reagent into the filter part 220. The lysis reagent is supplied into the filter part 220 during a second preset time. When the second present time elapses, the lysis agent supply device 370 stops operating. In operations S14 and S15, the lysis reagent may lyses the microbial particles collected onto the filter part 220 to extract the ATP, and the extracted ATP reacts with the luminous material applied onto the filter part 220 to emit predetermined light.

The filter driving part 250 operates. When the filter driving part 250 operates, the filter case 210 and the filter part 220 move so that the one area of the filter part 220 onto which the microbial particles are collected is disposed at one side of the luminescence measurement device 300. Thus, the one area of the filter part 220 may face the light receiving part 320. Also, in operation S16, the other area of the filter part 220 may be disposed to communicate with the microbial particle passage 127.

The luminescence measurement device 300 operates, and the light receiving part 320 detects the amount or intensity of the light emitted from the filter part 220. The amount of intensity of the light may be proportional to the microbial concentration. That is, when the light has a great amount or intensity, it may be recognized that the microbial concentration is high in proportional to the great amount or intensity of the light. Also, when the light has a small amount or intensity, it may be recognized that the microbial concentration is low in proportional to the small amount or intensity of the light.

The control part 450 may display information relating to the microbial concentration on the display part 420 on the basis of the information with respect to the amount or intensity of the light transmitted from the light receiving part 320. For example, in operations S17 and S18, the different colors of lighting parts may be activated in the display part 420.

Like this, since the process for collecting the microbial particles and the luminescence measurement process are automatically and successively performed, the airborne microbial measurement process may be easily conducted. Also, since the information relating to the microbial concentration is displayed on the display part, a user may easily recognize the airborne microbial concentration.

INDUSTRIAL APPLICABILITY

According to the airborne microbial measurement apparatus and method, the airborne microbial particles in the air may be automatically separated from the air through the virtual impactor structure without manually sampling the airborne microbial particles collected onto the collection plate by the user, and thus the process for separating particles may be easily performed to reduce the time taken to perform the process. Therefore, industrial applicability is significantly high.

The invention claimed is:

1. An airborne microbial measurement apparatus comprising:
    a particle separation device comprising an introduction part for introducing air and a nozzle part disposed on one side of the introduction part;
    a microbial particle passage through which microbial particles in the air passing through an inner passage of the nozzle part flow;
    an air particle passage through which air particles in the air passing through an outer space of the nozzle part flow;
    a collection device communicating with the microbial particle passage and comprising a filter part onto which the microbial particles are collected and a filter case in which the filter part is accommodated; and
    a luminescence measurement device comprising a light receiving device, the luminance measurement device being disposed on one side of the collection device to detect an amount or intensity of light emitted from the microbial particles collected onto the filter part; and
    a light receiving device detecting the amount of light emitted from the microbial particles collected onto the filter part,
    wherein the filter case comprises a plurality of filter holes defined in the filter case to expose the filter part to air from outside of the filter case, the plurality of filter holes comprising a first filter hole in communication with the microbial particle passage and a second filter hole that faces the light receiving device.

2. The airborne microbial measurement apparatus according to claim 1, further comprising:
    a pump generating a flow of the microbial particles in the microbial particle passage; and
    a blower fan generating a flow of the air particles in the air particle passage.

3. The airborne microbial measurement apparatus according to claim 1, wherein the nozzle part comprises:
    an inlet into which the microbial particles in the air are introduced; and
    an outlet through which the microbial particles are discharged to the microbial particle passage.

4. The airborne microbial measurement apparatus according to claim 3, wherein the inlet is disposed to be spaced apart from the introduction part in one direction, and
    the air particles are introduced into the air particle passage through a space between the inlet and the introduction part.

5. The airborne microbial measurement apparatus according to claim 3, wherein the introduction part comprises a plurality of slits, and
    the nozzle part is provided in plurality to corresponding to the number of plurality of slits.

6. The airborne microbial measurement apparatus according to claim 3, further comprising a partition plate having a communication hole to which the outlet of the nozzle part is coupled and separating the microbial particle passage from the air particle passage.

7. The airborne microbial measurement apparatus according to claim 1, further comprising a filter driving part rotating the filter part or the filter case,
    wherein, when the filter driving part operates in a state where the first filter hole communicates with the microbial particle passage, the second filter hole is disposed to communicate to the microbial particle passage.

8. The airborne microbial measurement apparatus according to claim 7, wherein, when the filter driving part operates in the state where the first filter hole communicates with the microbial passage, the first filter hole is disposed to face the light receiving part.

9. The airborne microbial measurement apparatus according to claim 1, further comprising:
    a lysis agent supply device for supplying a lysis reagent to the filter part; and
    a luminous material disposed on the filter part.

10. The airborne microbial measurement apparatus according to claim 1, further comprising a display part for displaying information with respect to a concentration of the microbial particles on the basis of information relating to the amount or intensity of the light detected by the luminescence measurement device.

* * * * *